Figure 1:
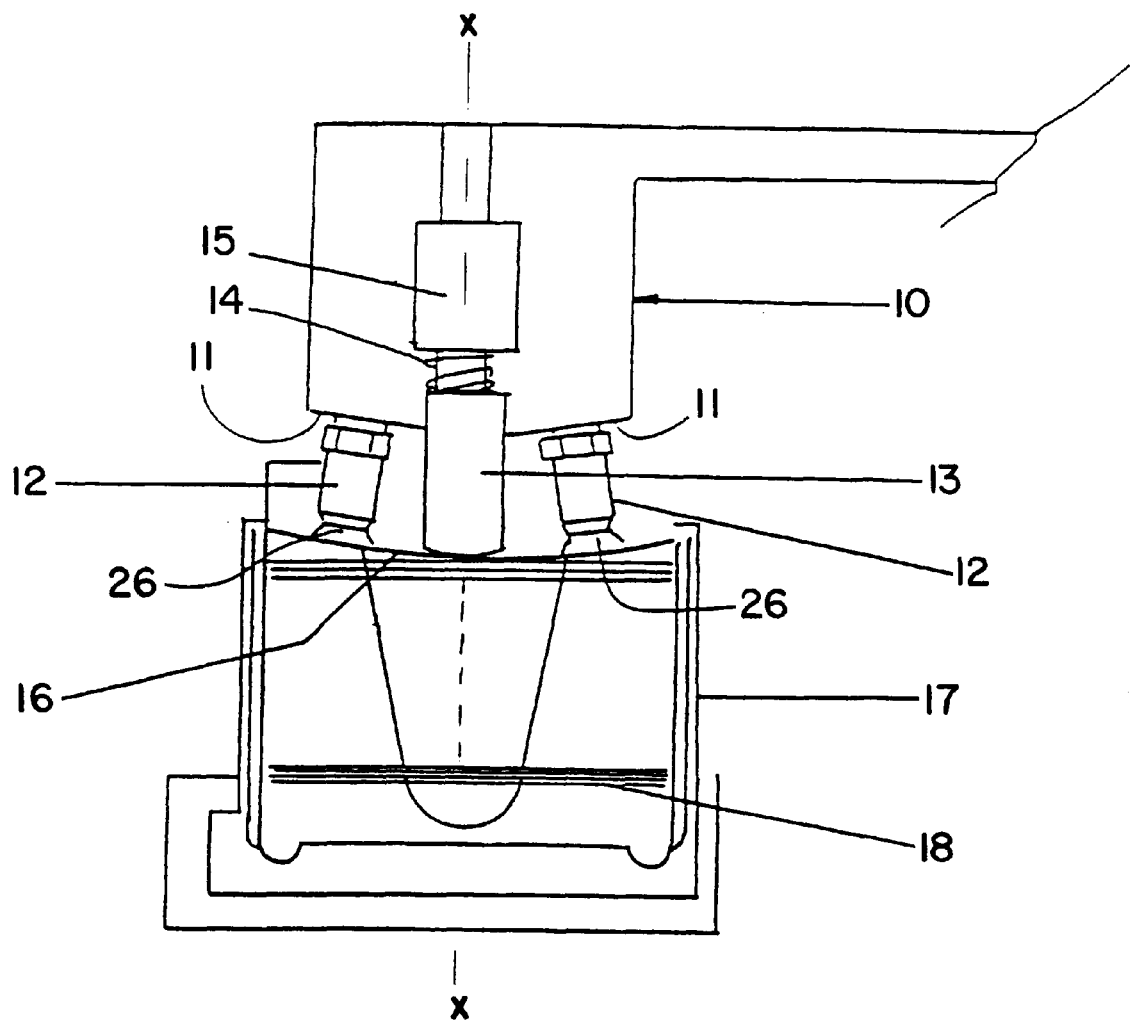

United States Patent [19]
Elliott

[11] Patent Number: 5,989,386
[45] Date of Patent: Nov. 23, 1999

[54] COVERSLIP PICK-UP AND LAYDOWN APPARATUS

[75] Inventor: Stuart Stanley Elliott, St Kilda, Australia

[73] Assignee: Vision Instruments Ltd., Victoria, Australia

[21] Appl. No.: 08/981,057

[22] PCT Filed: Jun. 14, 1996

[86] PCT No.: PCT/AU96/00357

§ 371 Date: Dec. 15, 1997

§ 102(e) Date: Dec. 15, 1997

[87] PCT Pub. No.: WO97/00461

PCT Pub. Date: Jan. 3, 1997

[30] Foreign Application Priority Data

Jun. 15, 1995 [AU] Australia .................................. PN3574

[51] Int. Cl.[6] .......................... B32B 31/04; G02B 21/34; B65H 3/08; B65H 3/46
[52] U.S. Cl. .......................... 156/344; 156/285; 156/556; 156/584; 221/33
[58] Field of Search .................................. 156/285, 310, 156/344, 538, 539, 556, 578, 584; 221/33

[56] References Cited

U.S. PATENT DOCUMENTS

| | | |
|---|---|---|
| 3,480,504 | 11/1969 | Good et al. . |
| 3,833,449 | 9/1974 | Johnson .................................. 156/556 |
| 3,930,928 | 1/1976 | Tapert . |
| 4,033,809 | 7/1977 | Tipton .................................. 156/578 X |
| 4,171,241 | 10/1979 | Henderson et al. ...................... 156/556 |
| 4,190,472 | 2/1980 | Slonicki .............................. 156/578 X |
| 4,203,797 | 5/1980 | Stormby . |
| 4,428,793 | 1/1984 | Sato et al. . |
| 4,455,188 | 6/1984 | Stormby . |
| 4,790,640 | 12/1988 | Nason . |
| 5,580,414 | 12/1996 | Ljungmann .......................... 156/556 X |

FOREIGN PATENT DOCUMENTS

| | | |
|---|---|---|
| 2 216 594 | 8/1974 | France . |
| 1 562 643 | 3/1980 | United Kingdom . |
| 1 597 954 | 9/1981 | United Kingdom . |
| 94/14097 | 6/1994 | WIPO . |
| 95/20176 | 7/1995 | WIPO . |

*Primary Examiner*—Curtis Mayes
*Attorney, Agent, or Firm*—Pillsbury Madison & Sutro LLP

[57] ABSTRACT

A coverslip pick-up and transfer head comprises a pair of spaced suction cups which are angled downwardly and outwardly. A spring loaded plunger in an extended condition extends below the suction cups such that when a coverslip is help by the suction cups it is flexed in a concave shape. A solenoid, when energized, retracts the plunger against the spring force. In use a coverslip magazine containing a stack of coverslips is raised under the head causing the plunger to retract until the suction cups contact the coverslips. Vacuum is applied to the suction cups and the magazine lowered whereby the coverslip is held by the suction cups and flexed into a concave shape. The solenoid is energized momentarily causing the plunger the retract and extend thereby delivering a gentle flexural pulse to the coverslip causing any further coverslip adhered to the underside of the top coverslip to be released and returned to the magazine. A coverslip laydown head includes a pivotal lever which is spring biased to provide a progressive force along the coverslip as it is laid on a slide at an ever increasing angle to thereby cause mountant on the slide to spread evenly over the slide with a uniform wavefront.

9 Claims, 2 Drawing Sheets

COVERSLIP PICK-UP AND LAYDOWN APPARATUS

This invention relates to an instrument for automatically applying coverslips to microscopic specimen slides in the field of histology and pathology. More particularly the invention relates to a method and apparatus, within such an instrument, for reliably lifting and separating a single glass coverslip from a stack of coverslips. In an alternative form the invention relates to a method and apparatus for mounting a coverslip onto a slide in a manner which produces a higher percentage of acceptable samples than has been previously achievable.

A machine of the kind in question is described in Applicant's earlier patent application No. PCT/AU95/00035 and the present invention relates to improvements in the lifting and separating apparatus and the laydown apparatus described in the earlier application.

Whilst the laydown apparatus described in the earlier application achieved a relatively high percentage of void free coverslipped slides this result has been achieved at the expense of excess mountant, which is undesirable for obvious reasons. Furthermore, whilst the method and apparatus for picking up coverslips from the top of a stack of coverslips, as described in the earlier application, is generally successful in separating a single coverslip from the stack the number of steps involved in the method and the fact that in some cases the coverslips are bonded together so strongly in the stack that more than one is picked up at a time is deleterious to the machine operation and causes inconvenience to the user.

Accordingly it is an object of the present invention to provide an improved coverslip laydown method and apparatus which uses less mountant and which results in a higher percentage of void free coverslipped slides.

A further object of the invention is to provide an improved method and apparatus for removing a single coverslip from a stack of coverslips.

Thus the invention provides a method of laying a coverslip on a slide including placing the coverslip over the slide with a first end of the coverslip in contact with the slide and the plane of the coverslip at an acute angle to the plane of the slide, moving the coverslip towards the slide whilst maintaining the other end of said coverslip at said angle whereby said coverslip is caused to curve away from said slide as it is progressively brought into contact with the slide, and providing an additional pressure between said coverslip and slide commencing at said first end and moving towards said other end as the coverslip is brought into contact with the slide to progressively squeeze the coverslip against the slide.

Another form of the invention provides apparatus for laying a coverslip on a slide, said apparatus comprising a laydown head adapted for movement towards and away from a slide, holding means on said head for holding a coverslip such that the plane of the coverslip is inclined relative to said axis and a pivotally mounted pressure pad on said head, the location of the holding means and pressure pad being such that when a coverslip is held by the holding means adjacent one end of the coverslip and the head is moved towards a slide, the other end of the coverslip contacts the slide and the plane of the coverslip is at an acute angle to the plane of the slide, further movement of the head towards the slide causing the coverslip to curve away from said slide as it is progressively brought into contact with the slide and said pressure pad providing additional pressure between said coverslip and slide commencing at said other end and moving towards said one end.

A still further form of the invention provides a method of lifting and separating a single coverslip from a stack of coverslips comprising raising the ends of a top coverslip of the stack whilst applying a downward force midway between said ends thereby flexing the coverslip, moving the top coverslip from the stack and momentarily removing and restoring said downward force to provide a flexural pulse to said top coverslip.

A still further form of the invention winch may be preferred provides a coverslip transfer head for picking up a coverslip from the top of a stack of coverslips, said transfer head comprising a plunger arranged between two spaced suction cups such that when the plunger is in an extended position over a stack of coverslips the plunger extends vertically downwardly beyond the lowermost position of the suction cups, said suction cups being inclined outwardly and downwardly relative to the vertical axis of the plunger such that when a coverslip is held by the two suction cups and the plunger is extended, the coverslip is flexed in a concave configuration, and a solenoid and a spring associated with said plunger for moving said plunger in opposite directions, respectively.

Figure 2A:
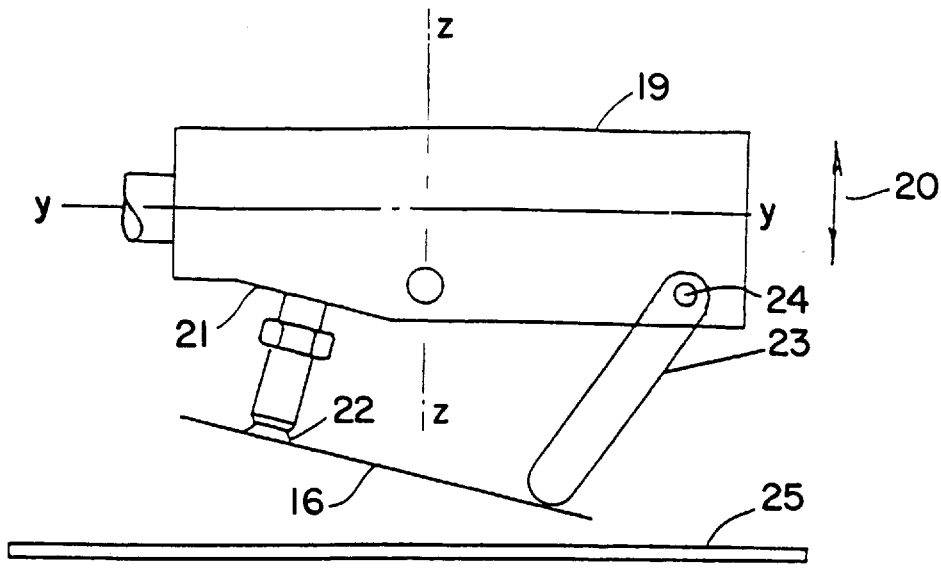
Figure 2B:
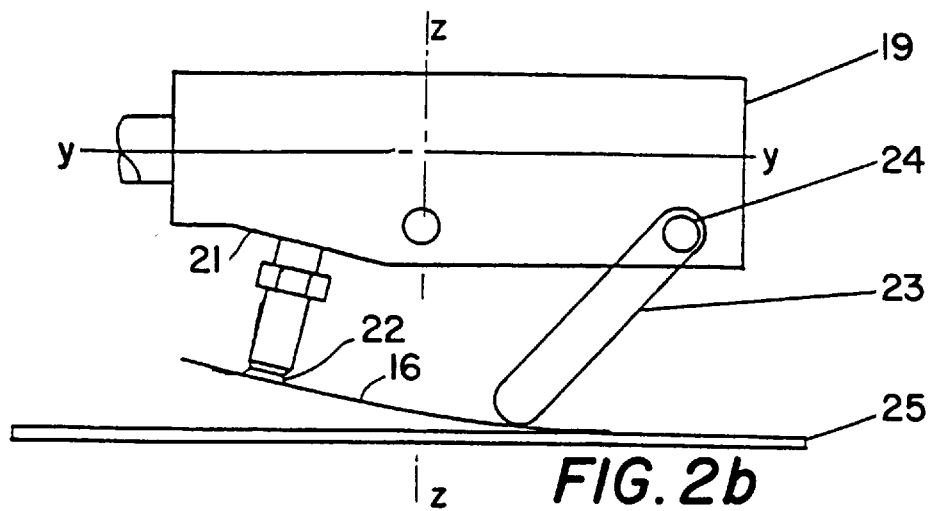
Figure 2C:
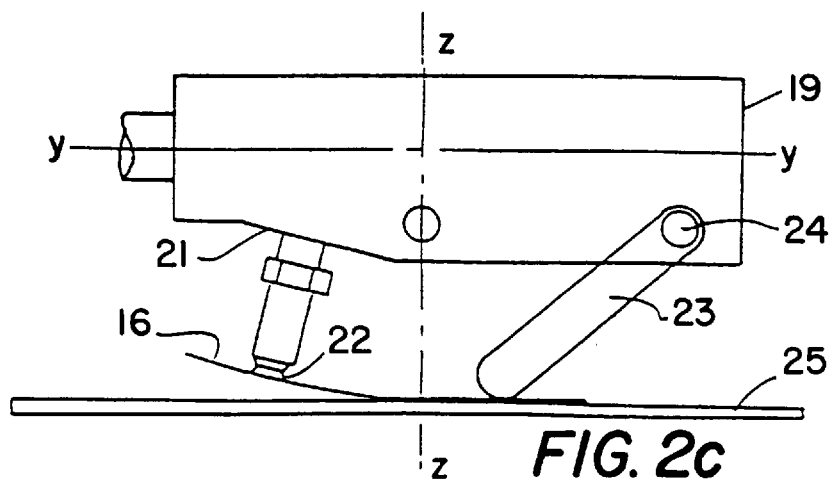

In order that the invention may be more readily understood particular embodiments will now be described with reference to the accompanying figures wherein:

FIG. 1 is a schematic elevation of a pick-up and transfer head according to an embodiment of the invention; and FIGS. 2a–2c are schematic side elevations of a coverslip lay-down head according to an embodiment of the invention, showing the head in various positions in the course of laying a coverslip on a slide.

Referring now to FIG. 1 the pick-up and transfer head 10 is shown to have inclined surfaces 11 on the underside thereof with a suction cup arrangement 12 mounted on each surface 11. As a consequence of the inclination of the surfaces 11 the suction cup arrangement 12 extend outwardly and downwardly from the transfer head 10 relative to a central vertical axis x—x. Each suction cup arrangement 12 is is provided with a suction cups 26.

A plunger 13 is mounted on the transfer head 10 and extends along the vertical axis. The plunger 13 is biased by spring 14 into a downward or lowermost position as shown in FIG. 1. A solenoid 15 is provided on the plunger 13 whereby actuation of the solenoid by an electric pulse causes the plunger 13 to retract against the force of spring 14 to an upper or retracted position (not shown) wherein the lowermost point of the plunger 13 is vertically above the plane of the suction cups 26. In other words in the retracted position the plunger 13 has little or no contact with a coverslip 16 being held by the suction cusps 26.

In FIG. 1 there is shown a coverslip magazine 17 which contains a stack 18 of coverslips and the magazine 17 is shown in a raised position enabling the uppermost coverslip to be contacted by the suction cups 26.

In operation of an instrument incorporating the pick-up and transfer head 10 the coverslip magazine 17 containing a stack 18 of coverslips is raised until the top coverslip comes into contact with the bottom end of the plunger 13 and then the suction cups 26. A vacuum is then applied to the suction cups 26 which firmly grip the top coverslip 16 adjacent the respective ends thereof. The force of the spring 14 and the angular orientation of the suction cups causes the coverslip 16 to flex in a concave configuration. Once in this position the magazine 17 is retracted downwardly and the top coverslip is retained by the pick-up and transfer head 10. As the coverslip magazine 17 is retracted downwards the solenoid 15 is energised momentarily causing the plunger to lift against the force of spring 14. The solenoid is then de-energised which releases the plunger causing it to deliver a gentle flexural pulse to the coverslip 16. This has the effect of breaking the adhering bond between the coverslip 16 and any further coverslip which may be adhered to the underside of the top coverslip 16. This allows the underneath coverslip to return to the magazine to be ready for the next pick-up cycle.

Referring now to FIGS. 2a, 2b and 2c there is shown a lay-down head 19 for laying a coverslip 16 on a slide 25 in a manner which facilitates use of a minimal amount of mountant and less probability of void formation between the coverslip and slide. The lay-down head 19 is rotatable about axis y—y and is also moveable vertically up and down in the direction of the arrow 20 shown in FIG. 2a. The lay-down head 19 has an inclined undersurface 21 from which depends a suction cup 22 which is inclined at an angle to the vertical axis z—z of the lay-down head 19. A pivotal lever 23 is mounted on the lay-down head 19 and is spring biased by a spring (not shown) in a direction anti-clockwise as viewed in FIGS. 2a–2c inclusive. The lever 23 is pivotally mounted on shaft 24 and assumes a rest position as shown in FIG. 2a by means of a stop (not shown) on the lay-down head 19. The lower end of the lever 23 incorporates a pressure pad in the form of a Teflon head (not shown) which reduces friction when the head slides along a coverslip as will become apparent hereinbelow.

A latch mechanism (also not shown) is provided on the lay-down head 19 to latch the lever 23 in a pivoted position clockwise from the initial position (as viewed in FIGS. 2a–2c) and approximately as shown in FIG. 2c. Detaching of the lever 23 occurs when the lay-down head 19 is rotated about the axis y—y through 180° to receive a further coverslip which is delivered to the lay-down head 19 by the pick-up and transfer head 10.

The major problem in laying the coverslip 16 on the slide 25 is that voids occur in the mountant as it is spread over the slide 25 and of course any such voids effect the ability to microscopically observe the specimen contained on the slide 25. Research by the present applicants has observed that void free results are, in the main, obtained by controlling the shape of the advancing mountant "wavefront" as the coverslip and slide are gradually brought together. The present invention achieves a uniformly advancing wave-front, thereby avoiding creation of voids, by a combination of the manner in which the mountant is applied to the slide and the manner in which the coverslip is laid down onto the slide.

Specifically, the mountant (not shown) is applied in a thin strip or streak up the centre of the slide (rather than a blob at one end of the slide) and, by virtue of the angled suction cup 22 and the spring assisted pressure pad provided on lever 23, the mountant is caused to advance along the slide 25 with a uniform wavefront extending across the width of the slide. The action of the pressure pad at the end of lever 23 is to progressively squeeze the coverslip against the slide as the lay down action proceeds. The line of action of the pressure pad moves up the coverslip creating a greater curvature of the coverslip and therefore a uniformly advancing wavefront in the mountant. This occurs as the lay-down head 19 moves downwardly towards the slide 25 causing the suction cup 22 to place the coverslip 16 on the slide. The use of the spring assisted pressure pad (lever 23) has enabled a considerable reduction in the quantity of mountant required to ensure a void free result. Whereas in applicants previous invention as described in Application No. PCF/AU95/00035 a central streak containing about 115 ml of mountant was required in order to achieve acceptable results, the invention described herein achieves even better results (a higher percentage of acceptable products) using only about 30 ml of mountant. The width of the pressure pad is about 15 mm which is considerably less than the width of the coverslip which is approximately 26 mm.

It should be apparent to persons skilled in the art that the present invention provides considerable improvements over prior art instruments of the kind in question. The unique pick-up and transfer head 10 provides a simple operation for ensuring that only one coverslip is selected from a stack of coverslips during each cycle of machine operation by providing a flexural pulse which breaks the adhering bond between the top coverslip and the next coverslip in the stack. Furthermore, the provision of a spring assisted pressure pad that works in conjunction with an angled suction cup on the lay-down head ensures a greater curvature of the coverslip as it is laid onto the slide and the combined action progressively squeezes the coverslip against the slide as the lay-down action proceeds. The mountant therefore proceeds in a uniform wavefront and the likelihood of voids occurring in the mountant is considerably reduced.

It should be also mentioned that the parallel operation of the pick-up and transfer head 10 and the lay-down head 19 allows multiple activities to occur simultaneously which facilitates greater machine throughput. This results in a more efficient instrument for automatically applying coverslips to microscopic specimen slides.

I claim:

1. A method of lifting and separating a single coverslip from a stack of coverslips comprising raising the ends of a top coverslip of the stack whilst applying a downward force midway between said ends thereby flexing the coverslip and subsequently moving the top coverslip from the stack, characterised in that, said method further includes momentarily removing and restoring said downward force to provide a flexural pulse to said top coverslip.

2. A method according to claim 1, characterised in that, said raising of the ends of the top coverslip is effected by angled suction cups and said downward force is provided by a spring load plunger having a solenoid to overcome the spring force.

3. Apparatus for laying a coverslip on a slide, said apparatus comprising a laydown head adapted for movement towards and away from a slide, and holding means on said head for holding said coverslip, characterised in that, said holding means holds said coverslip such that the plane of the coverslip is inclined relative to the plane of said slide, a pivotally mounted pressure pad on said head, the location of the holding means and pressure pad being such that when a coverslip is held by the holding means adjacent one end of the coverslip and the head is moved towards said slide, the other end of the coverslip contacts the slide and the plane of the coverslip is at an acute angle to the plane of the slide, further movement of the head towards the slide causes the coverslip to curve away from said slide as it is progressively brought into contact with the slide, and said pressure pad provides additional pressure between said coverslip and slide commencing at said other end and moving towards said one end.

4. Apparatus according to claim 3 wherein said holding means is a suction cup, characterised in that, said pressure pad is mounted at the end of a spring biased pivotal arm.

5. Apparatus according to claim 4, characterised in that, a latch is provided on said head to latch said arm in a pivoted position as the head moves towards said slide.

6. Apparatus according to claim 5, characterised in that, said suction cup is inclined relative to said axis and said pressure pad is formed of the material sold under the trademark TEFLON.

7. Apparatus according to claim 6, characterised in that, said head is rotatable through 180° from a laydown position to a substantially inverted position which enables the head to receive a coverslip, said rotation also actuating said latch to release said arm from said pivoted position.

8. A coverslip transfer head for picking up a coverslip from the top of a stack of coverslips, characterised in that, said transfer head comprises a plunger arranged between two spaced suction cups such that when the plunger is in an extended position over a stack of coverslips the plunger extends vertically downwardly beyond the lowermost position of the suction cups, said suction cups being inclined outwardly and downwardly relative to the vertical axis of the plunger such that when a coverslip is held by the two suction cups and the plunger is extended the coverslip is flexed in a concave configuration, and a solenoid and a spring associated with said plunger for moving said plunger in opposite directions, respectively.

9. A coverslip transfer head as defined in claim 8, characterised in that, said spring forces the plunger into said extended position and said solenoid withdraws said plunger against the force of said spring to a retracted position wherein the plunger is above the level of a plane through said suction cups.

* * * * *